United States Patent [19]
Werbitzky et al.

[11] Patent Number: 6,022,974
[45] Date of Patent: Feb. 8, 2000

[54] PROCESS FOR THE PRODUCTION OF 2-CHLORO-5-CHLOROMETHYL-PYRIDINE

[75] Inventors: Oleg Werbitzky; Philipp Studer, both of Visp, Switzerland

[73] Assignee: Lonza Ltd., Gampel/Valais, Switzerland

[21] Appl. No.: 08/059,384

[22] Filed: May 11, 1993

[30] Foreign Application Priority Data

May 12, 1992 [CH] Switzerland ............... 1518/92

[51] Int. Cl.[7] ............... C07D 211/72; C07D 211/70; C07D 211/78
[52] U.S. Cl. ............... 546/345; 546/315; 546/318; 546/344
[58] Field of Search ............... 546/315, 318, 546/344, 345

[56] References Cited

U.S. PATENT DOCUMENTS

| | | | |
|---|---|---|---|
| 4,778,896 | 10/1988 | Gallenkamp | 546/304 |
| 4,804,763 | 2/1989 | Franklin | 546/345 |
| 4,927,938 | 5/1990 | Lindel | 546/315 |
| 4,958,025 | 9/1990 | Jelich | 546/345 |
| 4,990,622 | 2/1991 | Jelich | 546/345 |
| 5,010,201 | 4/1991 | Kaufmann et al. | 546/316 |
| 5,116,993 | 5/1992 | Jelich | 546/345 |
| 5,198,549 | 3/1993 | Gunther | 546/345 |
| 5,233,043 | 8/1993 | Jelich | 546/301 |

FOREIGN PATENT DOCUMENTS

| | | |
|---|---|---|
| 0172595 | of 1986 | European Pat. Off. . |
| 0260485 | of 1988 | European Pat. Off. . |
| 0373463 | of 1989 | European Pat. Off. . |
| 0373464 | of 1989 | European Pat. Off. . |
| 0370317 | of 1990 | European Pat. Off. . |
| 0393453 | of 1990 | European Pat. Off. . |
| 0458109 | of 1991 | European Pat. Off. . |

OTHER PUBLICATIONS

J. B. Hendrickson, *Organic Chemistry*, 3rd Edition, p. 782, 1970.

Primary Examiner—D. Margaret Seaman
Attorney, Agent, or Firm—Fisher, Christen & Sabol

[57] ABSTRACT

A process for the production of 2-chloro-5-chloromethylpyridine of the formula:

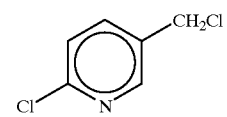

I starting from 6-hydroxynicotinic acid of the formula:

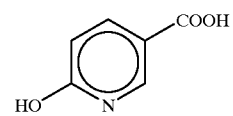

II

In this way 6-hydroxynicotinic acid is reacted with an acid chloride to 6-hydroxynicotinoyl chloride of the formula:

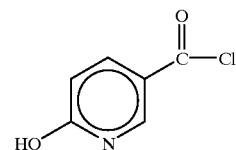

III

The latter is then catalytically hydrogenated with hydrogen to 6-hydroxy-5-hydroxymethylpyridine of the formula:

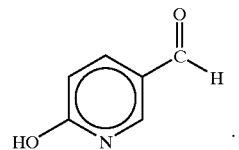

IV

The latter is then catalytically hydrogenated with hydrogen to 2-hydroxy-5-hydroxymethylpyridine of the formula:

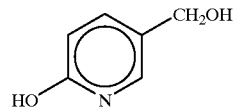

V which is then chlorinated to the end product according to formula I.

16 Claims, No Drawings

PROCESS FOR THE PRODUCTION OF 2-CHLORO-5-CHLOROMETHYL-PYRIDINE

BACKGROUND OF THE INVENTION

1. Field Of The Invention

The invention relates to a process for the production of 2-chloro-5-chloromethyl-pyridine of the formula:

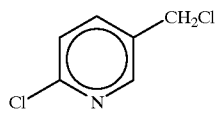

I starting from 6-hydroxynicotinic acid.

2. Background Art

Until now several expensive processes for the production of 2-chloro-5-chloromethyl-pyridine, which is sometimes abbreviated below as CCPM, have been known. For example, both European Published Patent Application Nos. 373463 and 373464 describe a process for the production of CCPM starting from nicotinic acid. Both applications describe a 5-step process according to the following reaction diagram:

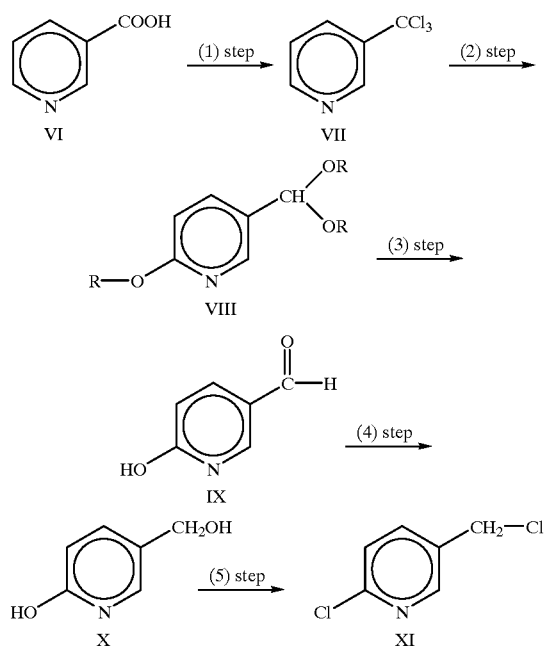

The drawbacks of these two processes are that the desired product is only produced by an expensive 5-step synthesis and, accordingly, CCPM is obtained in a small yield relative to the feedstock nicotinic acid. Another drawback is that a large amount of salts accumulates as waste in these processes.

BROAD DESCRIPTION OF THE INVENTION

The main object of the invention is to eliminate these drawbacks and to provide a more economical and technically less expensive process for the production of 2-chloro-5-chloromethyl-pyridine. Other objects and advantages of the invention are set out herein or are obvious herefrom to one skilled in the art.

The objects and advantages are achieved by the process of the invention.

According to the invention the process is performed so that in the first step, 6-hydroxynicotinic acid of formula:

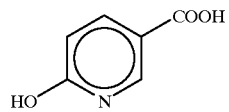

II is reacted with an acid chloride to 6-hydroxynicotinoyl chloride of the formula:

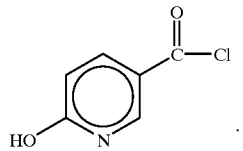

III

The latter is catalytically hydrogenated in the second step with hydrogen to 6-hydroxynicotinic acid aldehyde of the formula:

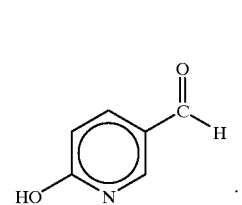

IV

Then the 6-hydroxynicotinic acid aldehyde is catalytically hydrogenated in the third step with hydrogen to 2-hydroxy-5-hydroxymethylpyridine of the formula:

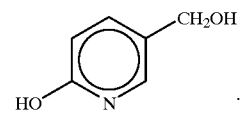

V

The latter then is further chlorinated in the fourth step to the end product, 2-chloro-5-chloromethyl-pyridine according to formula I.

2-Chloro-5-chloromethyl-pyridine is an important intermediate product for the production of insecticides [European Published Patent Application No. 373464].

DETAILED DESCRIPTION OF THE INVENTION

A special advantage of the process according to the invention is that the feedstock, the 6-hydroxynicotinic acid, can be converted into CCPM under simple reaction conditions with easily accessible reagents.

The first step, the reaction of 6-hydroxynicotinic acid to 6-hydroxynicotinoyl chloride with an acid chloride is in itself known according to Swiss Patent No. 654,754. Suitable as the acid chlorides for the first step are, for example, thionyl chloride, phosphoroxy chloride and phosphorus pentachloride, preferably thionyl chloride. The acid chlorides are usually used in excess relative to the stoichiometric ratio. Suitably the acid chlorides are used in an amount of 5 to 1 mol, preferably of 3.5 to 1 mol, per mol of the 6-hydroxynicotinic acid.

Suitably the first step is performed in the presence of a tertiary amine as a catalyst. As the tertiary amines, for example, pyridines, that are optionally alkyl substituted, can be used. Preferably pyridine is used as the catalyst. The catalysts are suitably applied in an amount of 0.01 to 0.3 mol, relative to 1 mol of the 6-hydroxynicotinic acid. The reaction temperature in the first step is suitably in a range between 0° and 80° C. As solvents for the first step, inert solvents, such as, methylene chloride, chloroform and carbon tetrachloride, are suitable.

However, it was found that if acetonitrile is used as the inert solvent in the first step, the amount of the catalyst necessary for the reaction can be considerably reduced. Accordingly, in a preferred embodiment, the first step is performed in acetonitrile as the inert solvent. Then, the catalyst is preferably used in an amount of 0.001 to 0.01 mol, relative to 1 mol of the 6-hydroxynicotinic acid. Suitably then the first step is performed at a temperature of 0° to 100° C., preferably of 60° to 80° C.

After a usual reaction time of 0.2 to 2 hours, 6-hydroxynicotinoyl chloride can then be isolated according to methods usual to one skilled in the art.

The second step, the reaction of 6-hydroxy-nicotinoyl-chloride to 6-hydroxynicotinic acid aldehyde takes place by catalytic hydrogenation with hydrogen. As the hydrogenation catalysts for the second step, noble metal catalysts, optionally on a suitable support, can be used. Palladium on activated carbon, particularly 5 to 10 percent by weight of palladium on activated carbon, is preferably used as the hydrogenation catalyst. The hydrogenation catalysts in the second step can be used in an amount of 0.01 to 0.1 mol, preferably of 0.03 to 0.05 mol, per mol of the 6-hydroxynicotinoyl chloride.

The second step can be performed at normal (atmospheric) pressure or at an elevated $H_2$ pressure. Preferably, the second step takes place at an elevated $H_2$ pressure of 3 to 20 bar. The reaction in the second step can take place with or without addition of a so-called auxiliary base. As the auxiliary base, tertiary amines, such as, triethylamine and 2,6-lutidine, can be used. Preferably, the second step is performed without an auxiliary base. Suitably the second step takes place in an inert solvent. Suitable inert solvents for the second step are, for example, acetonitrile, acetone, tetrahydrofuran and ethyl acetate. Preferably acetonitrile is used as the inert solvent in the second step. The reaction in the second step suitably takes place at a temperature of 0° to 150° C., preferably of 80° to 130° C.

After a usual reaction time of 2 to 10 hours, 6-hydroxynicotinic acid aldehyde can then be isolated after the second step according to methods usual to one skilled in the art.

The third step, the hydrogenation of 6-hydroxynicotinic acid aldehyde to 2-hydroxy-5-hydroxymethylpyridine also takes place catalytically with hydrogen. As the hydrogenation catalysts for the third step, noble metal, noble metal oxide or Raney catalysts, optionally on a suitable support, can be used. Preferably the third step, like the second step, is performed with palladium on activated carbon, especially with 5 to 10 percent by weight of palladium on activated carbon, as the hydrogenation catalyst. The amount of the hydrogenation catalyst in the third step is suitably between 0.001 and 0.01 mol, preferably between 0.001 and 0.005 mol, per mol of the 6-hydroxynicotinic acid aldehyde.

The third step can also take place like the second step at normal (atmospheric) pressure or at an elevated $H_2$ pressure. Preferably the hydrogenation takes place at an elevated $H_2$ pressure between 2 and 20 bars. The third step suitably takes place in a polar solvent. As the polar solvents, for example, water, methanol, ethanol, 2-propanol can be used; preferably water is used as the polar solvent. The reaction temperature in the third step suitably is between 0° and 150° C., preferably between 20° and 100° C.

After a usual reaction time of 0.2 to 2 hours, 2-hydroxy-5-hydroxymethylpyridine is then isolated according to methods usual to one skilled in the art.

The fourth step, the chlorination of 2-hydroxy-5-hydroxymethylpyridine to CCPM takes place with chlorination agents usual to one skilled in the art, such as, phosphorus pentachloride, phosphoroxy chloride and phosgene. Usually the chlorination agent is used in excess relative to the 2-hydroxy-5-hydroxymethylpyridine used, preferably in an amount of 2 to 5 mol, per mol of the 2-hydroxy-5-hydroxymethylpyridine. An inert solvent is suitably used as the solvent in the fourth step. As the inert solvent, for example, chloroform, methylene chloride, carbon tetrachloride and phosphoroxy chloride are suitable. Preferably the fourth step is performed dissolved in phosphoroxy chloride. The reaction temperature in the fourth step is suitably between 0° and 150° C., preferably between 80° and 120° C.

After a usual reaction time of 2 to 8 hours, CCPM is then obtained in good yield and purity according to methods usual to one skilled in the art.

EXAMPLE 1

Production of 6-hydroxynicotinoyl chloride 13.92 g (0.1 mol) of 6-hydroxynicotinic acid and 0.04 g (0.5 mmol) of pyridine were heated in 60 ml of acetonitrile to 80° C. 12.49 g (0.105 mol) of thionyl chloride was instilled and the reaction again stirred for 30 minutes at 80° C. After cooling, the precipitate was filtered off, washed twice each with 10 ml of cold acetonitrile and concentrated by evaporation in a vacuum. 13.38 g (0.085 mol) of 6-hydroxynicotinoyl chloride was obtained as a light yellowish powder, corresponding to a yield of 85 percent relative to the 6-hydroxynicotinic acid. Further data concerning the product was:

$^1$H-NRM: (CDCl$_3$, 300 MHz) δ in ppm: 8.44 (d, J=2.6 Hz, 1H, H-2); 8.01 (dd, J=2.6 Hz, J=9.7 Hz, 1H, H-4); 6.62 (d, J=9.7 Hz, 1H, H-5).

EXAMPLE 2

Production of 6-hydroxynicotinic acid aldehyde 13.35 g (0.086 mol) of 6-hydroxynicotinoyl chloride in 650 ml of acetonitrile was hydrogenated in an autoclave with 2.7 g of 5% Pd/C catalyst at 80° C. and 10 bar H$_2$. 4 hours after the end of the reaction the catalyst was filtered off and washed several times with hot water. The combined filtrates were concentrated by evaporation, and the residue was recrystallized from water. 7.94 g (64 mmol) of 6-hydroxynicotinic acid aldehyde was obtained as colorless crystals, corresponding to a yield of 74 percent relative to the 6-hydroxynicotinoyl chloride. The product had a melting point of 219° C. Further data concerning the product was:

$^1$H-NRM: (CDCl$_3$, 300 MHz) δ in ppm: 12.31 (s, br, 1H, OH) 9.59 (s, 1H, CHO); 8.25 (D, j=2.3 Hz, 1H, H-2); 7.75 (dd, J=9.6 Hz, J=2.4 Hz, 1H, H-4); 6.41 (d, J=9.6 Hz, 1H, H-5).

EXAMPLE 3

Production of 2-hydroxy-5-hydroxymethyl-pyridine 1.0 g (8.1 mmol) of 6-hydroxynicotinic acid aldehyde in 80 ml of water was hydrogenated in an autoclave with 50 mg of 5% Pd/C catalyst at room temperature and 10 bar H$_2$. 1 hour after the end of the reaction the catalyst was filtered off and the filtrate concentrated by evaporation. 0.96 g of a colorless solid was obtained, corresponding to a yield of 94 percent relative to the 6-hydroxynicotinic acid aldehyde. Further data concerning the product was:

$^1$H-NMR: (D$_2$O, 300 MHz) δ in ppm: 7.73 (dd, J=2.2 Hz, J=9.3, 1H, H-4); 7.52 (d, J=2.2 Hz, 1H, H-6); 6.63 (d, J=9.3 Hz, 1H, H-3); 4.48 (s, CH$_2$OH, 1H).

EXAMPLE 4

Production of 2-chloro-5-chloromethyl-pyridine

A solution of 2.5 g (20 mmol) of 2-hydroxy-5-hydroxymethylpyridine and 4.16 g of phosphorus pentachloride in 10 ml of phosphoryl chloride was stirred for 6 hours at 105° C. After cooling, 50 ml of chloroform was added, the excess chlorination reagent being hydrolyzed by careful addition of water. The organic phase was washed with NaHCO$_3$ solution, dried on NaSO$_4$ and concentrated by evaporation. The distillation of the oily residue at 16 mm and 120° C. yielded 3.08 g of 2-chloro-5-chloromethyl-pyridine as a colorless oil that solidified during the cooling. The latter corresponds to a yield of 95 percent relative to the 2-hydroxy-5-hydroxymethyl-pyridine. Further data concerning the product was:

$^1$H-NMR: (CDCl$_3$, 300 MHz) δ in ppm: 8.28 (d, J=2.3 Hz, 1H, H-6); 7.72 (dd, J=8.2 Hz, J=2.3 Hz, H-4); 7.34 (d, J=8.2 Hz, 1H, H-3); 4.58 (s, CH$_2$Cl, 2H).

What is claimed is:

1. A process for the production of 2-chloro-5-chloromethyl-pyridine of formula:

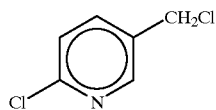

I comprising, in a first step, reacting 6-hydroxynicotinic acid of formula:

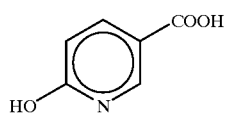

II with an acid chloride to 6-hydroxynicotinoyl chloride of formula:

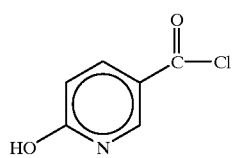

III in a second step, catalytically hydrogenating the 6-hydroxynicotinoyl chloride of formula III with hydrogen to 6-hydroxynicotinic acid aldehyde of formula:

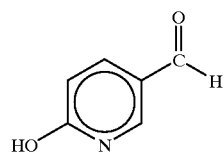

IV in a third step, catalytically hydrogenating the 6-hydroxynicotinic acid aldehyde of formula IV with hydrogen to 2-hydroxy-5-hydroxymethylpyridine of formula:

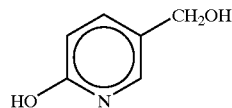

V and, in a fourth step, chlorinating the 2-hydroxy-5-hydroxymethylpyridine of formula V to the 2-chloro-5-chloromethyl-pyridine of formula I.

2. The process according to claim 1 wherein, in the first step, thionyl chloride is used as the acid chloride and acetonitrile is used as a solvent.

3. The process according to claim 2 wherein the reaction in the first step is performed in the presence of a tertiary amine, as a catalyst, in an amount of 0.001 to 0.01 mole, per mol of the 6-hydroxynicotinic acid.

4. The process according to claim 3 wherein the reaction in the first step is performed at a temperature of 0° to 100° C.

5. The process according to claim 4 wherein the hydrogenation in the second step is performed at a pressure of 3 to 20 bar and at a temperature of 0° to 150° C.

6. The process according to claim 5 wherein palladium on carbon is used as the hydrogenation catalyst in the second and third steps.

7. The process according to claim 6 wherein the reaction in the third step is performed at a pressure of 2 to 20 bar and at a temperature of 0° to 150° C.

8. The process according to claim 7 wherein the chlorination in the fourth step is performed with phosphorus pentachloride, phosphoroxy chloride or phosgene.

9. The process according to claim 8 wherein the chlorination in the fourth step is performed at a temperature of 0° to 150° C.

10. The process according to claim 1 wherein the reaction in the first step is performed in the presence of a tertiary amine, as a catalyst, in an amount of 0.001 to 0.01 mole, per mol of the 6-hydroxynicotinic acid.

11. The process according to claim 1 wherein the reaction in the first step is performed at a temperature of 0° to 100° C.

12. The process according to claim 1 wherein the hydrogenation in the second step is performed at a pressure of 3 to 20 bar and at a temperature of 0° to 150° C.

13. The process according to claim 1 wherein palladium on carbon is used as the hydrogenation catalyst in the second and third steps.

14. The process according to claim 1 wherein the reaction in the third step is performed at a pressure of 2 to 20 bar and at a temperature of 0° to 150° C.

15. The process according to claim 1 wherein the chlorination in the fourth step is performed with phosphorus pentachloride, phosphoroxy chloride or phosgene.

16. The process according to claim 1 wherein the chlorination in the fourth step is performed at a temperature of 0° to 150° C.

* * * * *